US011224517B2

(12) United States Patent
Langhorn et al.

(10) Patent No.: US 11,224,517 B2
(45) Date of Patent: Jan. 18, 2022

(54) MECHANICALLY COUPLED REVISION HIP SYSTEM AND METHOD

(71) Applicant: DEPUY SYNTHES PRODUCTS, INC., Raynham, MA (US)

(72) Inventors: Jason B. Langhorn, Warsaw, IN (US); Chase R. Maag, Warsaw, IN (US)

(73) Assignee: DEPUY SYNTHES PRODUCTS, INC., Raynham, MA (US)

( * ) Notice: Subject to any disclaimer, the term of this patent is extended or adjusted under 35 U.S.C. 154(b) by 174 days.

(21) Appl. No.: 16/452,877

(22) Filed: Jun. 26, 2019

(65) Prior Publication Data

US 2020/0405492 A1 Dec. 31, 2020

(51) Int. Cl.
*A61F 2/34* (2006.01)
*A61F 2/32* (2006.01)
*A61F 2/36* (2006.01)
*A61F 2/30* (2006.01)

(52) U.S. Cl.
CPC .......... *A61F 2/3609* (2013.01); *A61F 2/3094* (2013.01); *A61F 2/34* (2013.01); *A61F 2/3662* (2013.01); *A61F 2/30767* (2013.01); *A61F 2002/30616* (2013.01); *A61F 2002/3241* (2013.01)

(58) Field of Classification Search
CPC .................. A61F 2/3609; A61F 2/3662; A61F 2002/3448; A61F 2002/345; A61F 2/3094; A61F 2/30767; A61F 2002/30624; A61F 2002/30632; A61F 2002/30634; A61F 2002/30635; A61F 2002/3069; A61F 2/32; A61F 2/34; A61F 2/36
See application file for complete search history.

(56) References Cited

U.S. PATENT DOCUMENTS

| | | | |
|---|---|---|---|
| 3,641,590 A | 2/1972 | Michele | |
| 3,683,421 A | 8/1972 | Martinie | |
| 3,694,820 A | 10/1972 | Scales et al. | |
| 3,708,805 A | 1/1973 | Scales et al. | |
| 3,869,730 A * | 3/1975 | Skobel | A61F 2/30742 623/19.12 |
| 3,916,451 A * | 11/1975 | Buechel | A61F 2/32 623/23.4 |
| 4,003,095 A * | 1/1977 | Gristina | A61F 2/40 623/19.12 |
| 4,038,704 A | 8/1977 | Ring | |
| 4,040,130 A * | 8/1977 | Laure | A61F 2/4261 623/21.13 |
| 4,040,131 A | 8/1977 | Gristina | |

(Continued)

FOREIGN PATENT DOCUMENTS

AU 2003244030 A1 4/2004
EP 0664108 A2 7/1995
(Continued)

OTHER PUBLICATIONS

PCT International Search Report for International Application No. PCT/IB2020/054625, dated Aug. 12, 2020; 7 pages.

*Primary Examiner* — Alvin J Stewart
(74) *Attorney, Agent, or Firm* — Barnes & Thornburg LLP

(57) ABSTRACT

An acetabular hip implant includes a plurality of rings secured to an acetabular shell component. A method of fabricating a customized, patient-specific version of such an implant is also disclosed.

20 Claims, 6 Drawing Sheets

(56) References Cited

U.S. PATENT DOCUMENTS

| | | | |
|---|---|---|---|
| 4,229,841 A * | 10/1980 | Youm | A61F 2/4261 623/21.12 |
| 4,642,123 A * | 2/1987 | Noiles | A61F 2/32 623/22.2 |
| 4,731,088 A | 3/1988 | Collier | |
| 4,759,767 A | 7/1988 | Lacey | |
| 4,865,609 A | 9/1989 | Roche | |
| 4,911,719 A | 3/1990 | Merle | |
| 5,092,898 A * | 3/1992 | Bekki | A61F 2/32 623/22.16 |
| 5,282,865 A | 2/1994 | Dong | |
| 5,514,182 A | 5/1996 | Shea | |
| 5,556,434 A * | 9/1996 | Epstein | A61F 2/32 623/22.16 |
| 5,755,807 A | 5/1998 | Anstaett et al. | |
| 5,800,556 A * | 9/1998 | Sanders | A61F 2/4684 623/22.45 |
| 5,888,207 A * | 3/1999 | Nieder | A61F 2/32 623/23.15 |
| 5,888,211 A * | 3/1999 | Sanders | A61F 2/4684 623/22.4 |
| 6,002,859 A | 12/1999 | DiGioia, III et al. | |
| 6,042,611 A * | 3/2000 | Noiles | A61F 2/34 623/22.21 |
| 6,168,630 B1 * | 1/2001 | Keller | A61F 2/4261 623/21.11 |
| 6,375,684 B1 | 4/2002 | Kriek | |
| 6,629,999 B1 * | 10/2003 | Serafin, Jr. | A61F 2/384 623/20.15 |
| 6,953,478 B2 | 10/2005 | Bouttens et al. | |
| 7,011,686 B2 | 3/2006 | Ball et al. | |
| 7,022,140 B2 | 4/2006 | Novelli | |
| 7,108,720 B2 * | 9/2006 | Hanes | A61F 2/32 623/22.21 |
| 7,309,360 B2 | 1/2007 | Tornier et al. | |
| 7,179,298 B2 * | 2/2007 | Greenlee | A61F 2/32 623/22.16 |
| 7,344,565 B2 | 3/2008 | Seyer et al. | |
| 7,462,197 B2 | 12/2008 | Tornier et al. | |
| 7,465,319 B2 * | 12/2008 | Tornier | A61F 2/32 623/19.11 |
| 7,470,287 B2 | 12/2008 | Tornier et al. | |
| 7,611,539 B2 | 11/2009 | Bouttens et al. | |
| 7,678,150 B2 | 3/2010 | Tornier et al. | |
| 7,854,768 B2 | 12/2010 | Wiley et al. | |
| 7,887,544 B2 | 2/2011 | Tornier et al. | |
| 8,052,758 B1 | 11/2011 | Winslow | |
| 8,075,628 B2 | 12/2011 | Justin et al. | |
| 8,080,063 B2 | 12/2011 | Ferrand et al. | |
| 8,187,282 B2 | 5/2012 | Tornier et al. | |
| 8,277,511 B2 | 10/2012 | Tornier et al. | |
| 8,287,600 B2 | 10/2012 | Angibaud | |
| 8,303,665 B2 | 11/2012 | Tornier et al. | |
| 8,308,810 B2 * | 11/2012 | Meridew | A61F 2/34 623/22.19 |
| 8,361,157 B2 | 1/2013 | Bouttens et al. | |
| 8,449,620 B2 * | 5/2013 | Hakansson | A61F 2/4241 623/22.16 |
| 8,608,805 B2 | 12/2013 | Forrer et al. | |
| 8,647,387 B2 | 2/2014 | Winslow | |
| 8,690,951 B2 | 4/2014 | Baum et al. | |
| 8,864,834 B2 | 10/2014 | Boileau et al. | |
| 8,870,962 B2 | 10/2014 | Roche et al. | |
| 8,940,054 B2 | 1/2015 | Wiley et al. | |
| 8,974,536 B2 | 3/2015 | Walch et al. | |
| 9,060,862 B2 * | 6/2015 | Castro | A61F 2/32 |
| 9,089,435 B2 | 7/2015 | Walch et al. | |
| 9,132,016 B2 | 9/2015 | Flaherty et al. | |
| 9,233,003 B2 | 1/2016 | Roche et al. | |
| 9,283,075 B2 | 3/2016 | Wiley et al. | |
| 9,408,652 B2 | 8/2016 | Hassler et al. | |
| 9,433,507 B2 | 9/2016 | Reubelt et al. | |
| 9,474,619 B2 | 10/2016 | Reubelt et al. | |
| 9,545,312 B2 | 1/2017 | Tornier et al. | |
| 9,561,111 B1 * | 2/2017 | Goodman | A61F 2/4081 |
| 9,925,053 B2 * | 3/2018 | Overes | A61F 2/4014 |
| 10,420,649 B2 * | 9/2019 | Overes | A61F 2/32 |
| 10,596,005 B2 * | 3/2020 | Noel | A61F 2/34 |
| 2003/0114933 A1 | 6/2003 | Bouttens et al. | |
| 2004/0064190 A1 | 4/2004 | Ball et al. | |
| 2004/0068322 A1 * | 4/2004 | Ferree | A61F 2/385 623/23.39 |
| 2004/0186586 A1 | 9/2004 | Seyer et al. | |
| 2004/0193282 A1 * | 9/2004 | Hanes | A61F 2/32 623/22.21 |
| 2004/0230197 A1 | 11/2004 | Tornier et al. | |
| 2005/0154469 A1 | 7/2005 | Novelli | |
| 2005/0165490 A1 | 7/2005 | Tornier | |
| 2005/0256583 A1 | 11/2005 | Bouttens et al. | |
| 2005/0278030 A1 | 12/2005 | Tornier et al. | |
| 2005/0278032 A1 | 12/2005 | Tornier et al. | |
| 2005/0278033 A1 | 12/2005 | Tornier et al. | |
| 2006/0100713 A1 | 5/2006 | Ball | |
| 2006/0111788 A1 | 5/2006 | Ball | |
| 2006/0111789 A1 | 5/2006 | Ball | |
| 2006/0200248 A1 | 9/2006 | Beguin et al. | |
| 2007/0112430 A1 | 5/2007 | Simmen et al. | |
| 2007/0173945 A1 | 7/2007 | Wiley et al. | |
| 2007/0225817 A1 | 9/2007 | Reubelt et al. | |
| 2007/0225818 A1 | 9/2007 | Reubelt et al. | |
| 2007/0225821 A1 | 9/2007 | Reubelt et al. | |
| 2007/0250174 A1 | 10/2007 | Tornier et al. | |
| 2008/0183297 A1 | 7/2008 | Boileau et al. | |
| 2008/0228281 A1 | 9/2008 | Forrer et al. | |
| 2008/0294268 A1 | 11/2008 | Baum et al. | |
| 2009/0024221 A1 | 1/2009 | Ball | |
| 2009/0041534 A1 * | 2/2009 | Bushey | B25J 17/0275 403/57 |
| 2009/0112328 A1 | 4/2009 | Tornier et al. | |
| 2009/0187251 A1 | 7/2009 | Justin et al. | |
| 2010/0023068 A1 | 1/2010 | Bouttens et al. | |
| 2010/0087927 A1 | 4/2010 | Roche et al. | |
| 2010/0222886 A1 | 9/2010 | Wiley et al. | |
| 2010/0256770 A1 * | 10/2010 | Hakansson | A61F 2/4241 623/21.16 |
| 2011/0035014 A1 | 2/2011 | Forrer | |
| 2011/0098822 A1 | 4/2011 | Walch et al. | |
| 2011/0166661 A1 | 7/2011 | Boileau et al. | |
| 2011/0166662 A2 | 7/2011 | Forrer | |
| 2012/0004733 A1 * | 1/2012 | Hodorek | A61F 2/4081 623/19.11 |
| 2012/0053697 A1 * | 3/2012 | Palmer | A61F 2/3804 623/20.12 |
| 2012/0209398 A1 * | 8/2012 | Richardson | A61F 2/34 623/22.17 |
| 2012/0239147 A1 * | 9/2012 | Winkler | A61F 2/44 623/17.11 |
| 2013/0345822 A1 * | 12/2013 | Grostefon | A61F 2/34 623/22.16 |
| 2016/0135958 A1 | 5/2016 | Grostefon et al. | |
| 2016/0235539 A1 * | 8/2016 | Overes | A61F 2/32 |
| 2018/0116805 A1 * | 5/2018 | Johannaber | A61B 5/05 |
| 2018/0116808 A1 * | 5/2018 | Overes | A61F 2/3854 |
| 2018/0193156 A1 * | 7/2018 | Zajac | A61F 2/4609 |
| 2018/0311045 A1 * | 11/2018 | Noel | A61F 2/32 |
| 2019/0240031 A1 * | 8/2019 | Kimura | A61F 2/30734 |
| 2019/0269517 A1 * | 9/2019 | Palmer | A61F 2/3804 |
| 2020/0345517 A1 * | 11/2020 | Morrisey | A61F 2/4607 |

FOREIGN PATENT DOCUMENTS

| | | |
|---|---|---|
| EP | 0808617 A2 | 11/1997 |
| EP | 0966240 B1 | 10/2002 |
| EP | 1844737 A2 | 10/2007 |
| EP | 2042129 A1 | 4/2009 |
| EP | 2057971 A1 | 5/2009 |
| FR | 1122634 A | 9/1956 |
| FR | 2357235 A1 | 2/1978 |
| FR | 2744627 A1 | 8/1997 |
| FR | 2761878 A1 | 10/1998 |
| FR | 2899790 A1 | 10/2007 |
| JP | 04210353 A | 7/1992 |

(56) References Cited

FOREIGN PATENT DOCUMENTS

| | | | |
|---|---|---|---|
| JP | 05344714 | A | 12/1993 |
| JP | 2011502601 | A | 1/2011 |
| NL | 1005234 | C2 | 8/1998 |
| WO | 9834567 | A1 | 8/1998 |
| WO | 0241808 | A1 | 5/2002 |
| WO | 2009060006 | A1 | 5/2009 |
| WO | 2013148434 | A1 | 10/2013 |
| WO | 2015051476 | A1 | 4/2015 |

\* cited by examiner

MECHANICALLY COUPLED REVISION HIP SYSTEM AND METHOD

TECHNICAL FIELD

The present disclosure relates generally to prosthetic orthopaedic implants, and more particularly, to orthopaedic hip implants.

BACKGROUND

Many orthopaedic procedures involve the implantation of prosthetic devices to replace badly damaged or diseased joint tissue. Common orthopaedic procedures that involve prosthetic devices include total or partial hip, knee, and shoulder replacements. Hip replacement involves total or partial replacement of the hip ball and socket joint.

A total hip replacement procedure typically involves the implantation of two main component systems: a femoral component and an acetabular component. The femoral component includes a rigid stem that is anchored within the patient's femur and also includes a head that replaces the patient's natural femoral head. The acetabular component is implanted within the acetabulum of the patient and serves as a bearing surface for the head of the femoral component. The acetabular component generally includes an outer shell configured to engage the acetabulum of the patient and an inner bearing or liner coupled to the shell and configured to engage the femoral head. The femoral head and inner liner of the acetabular component form a ball and socket joint that approximates the natural hip joint.

SUMMARY

According to an illustrative embodiment, an acetabular hip implant includes an acetabular shell component configured to be implanted within an acetabulum of a patient, a first ring secured to the acetabular shell component, a second ring secured to the first ring, and a third ring secured to the second ring.

The first ring extends around a first longitudinal axis and includes an inner surface and an outer surface. The first ring defines (i) a first closed track extending circumferentially around the first ring and radially through the inner surface and the outer surface of the first ring, and (ii) a second closed track located opposite the first closed track and extending circumferentially around the first ring and radially through the inner surface and the outer surface of the first ring.

The second ring extends around a second longitudinal axis and includes an inner surface and an outer surface. The second ring also includes a first pin extending from the second ring along a first rotational axis into the first closed track, and a second pin extending from the second ring along the first rotational axis into the second closed track. The second ring defines (i) a third closed track extending circumferentially around the second ring and radially through the inner surface and the outer surface of the second ring, and (ii) a fourth closed track extending circumferentially around the second ring and radially through the inner surface and the outer surface of the second ring.

The third ring extends around a third longitudinal axis and includes a third and fourth pin. The third pin extends from the third ring along a second rotational axis into the third closed track and the fourth pin extends from the third ring along the second rotational axis into the fourth closed track.

The third ring is secured to a femoral stem component. An inner surface of the third ring is taper locked to the femoral stem component.

The third ring is operable to rotate relative to the second ring about the second rotational axis and the second longitudinal axis. The third ring is prevented from rotating relative to the second ring about any additional axis. The first closed track and the second closed track each extend circumferentially around the first ring a first distance. The third closed track and the fourth closed track each extend circumferentially around the second ring a second distance. In some embodiments, the first distance is a predetermined, patient-specific distance based on a desired range of motion for a patient's hip when the acetabular hip implant is implanted in the acetabulum of the patient. In some embodiments, the second distance is a predetermined, patient-specific distance based on a desired range of motion for a patient's hip when the acetabular hip implant is implanted in the acetabulum of the patient. In some embodiments, the first distance is equal to the second distance.

The acetabular hip implant includes a first pair of sleeves and a second pair a sleeves. The first pair of sleeves is configured to be secured to the first and second pins and sized and shaped to be positioned in the first and second closed tracks. The second pair of sleeves is configured to be secured to the third and fourth pins and sized and shaped to be positioned in the third and fourth closed tracks.

According to a further exemplary embodiment, an acetabular hip implant includes an acetabular shell component configured to be implanted within an acetabulum of a patient, a first ring secured to the acetabular shell component, a second ring secured to the first ring, and a third ring secured to the second ring.

The first ring extends around a first longitudinal axis. The second ring extends around a second longitudinal axis. The second ring is operable to rotate relative to the first ring about the first longitudinal axis and a first rotational axis perpendicular to the first longitudinal axis. The second ring is prevented from rotating relative to the first ring about any additional axis. The third ring extends around a third longitudinal axis. The third ring is operable to rotate relative to the second ring about the second longitudinal axis and a second rotational axis perpendicular to the second longitudinal axis. The third ring is prevented from rotating relative to the second ring about any additional axis. The third ring is secured to a femoral stem component.

The first ring includes an inner surface defining an inner diameter of the first ring and an outer surface opposite the inner surface. The second ring includes an inner surface defining an inner diameter of the second ring and an outer surface defining an outer diameter of the second ring that is less than the inner diameter of the first ring. The third ring includes an inner surface and an outer surface opposite the inner surface. The outer surface of the third ring defines an outer diameter of the third ring that is less than the inner diameter of the second ring.

The first ring defines a first pair of closed tracks extending circumferentially around the first ring a first distance and radially through the inner surface and the outer surface of the first ring. The second ring defines a second pair of closed tracks extending circumferentially around the second ring a second distance and radially through the inner surface and the outer surface of the second ring.

The first distance may be a predetermined, patient-specific distance based on a desired range of motion for a patient's hip when the acetabular hip implant is implanted in the acetabulum of the patient. The second distance may be a predetermined, patient-specific distance based on a desired range of motion for a patient's hip when the acetabular hip implant is implanted in the acetabulum of the patient.

The second ring includes a first pair of pins extending from the outer surface of the second ring along the first rotational axis into the first pair of closed tracks. The third ring includes a second pair of pins extending from the outer surface of the third ring along the second rotational axis into the second pair of closed tracks.

According to a further illustrative embodiment, a method of fabricating a customized patient-specific acetabular hip implant includes (i) determining a desired range of motion for a patient's hip, (ii) selecting a first ring having a first pair of closed tracks defined therein and extending circumferentially around the first ring a first patient-specific distance, (iii) selecting a second ring having a second pair of closed tracks defined therein and extending circumferentially around the second ring a second patient-specific distance, (iv) securing the second ring to the first ring, (v) securing a third ring of the customized, patient-specific acetabular hip implant to the second ring, and (vi) securing the first ring to an acetabular shell component implanted within the acetabulum of the patient.

The first patient-specific distance is based on the desired range of motion for the patient's hip. The second patient-specific distance is based on the desired range of motion for the patient's hip. The method of fabricating a customized, patient-specific acetabular hip implant includes securing a stem component to the third ring of the customized, patient-specific acetabular hip implant.

Other aspects and advantages of the present disclosure will become apparent upon consideration of the following drawings and detailed description, wherein similar structures have similar reference numbers.

BRIEF DESCRIPTION OF THE DRAWINGS

The detailed description particularly refers to the following figures, in which.

DETAILED DESCRIPTION OF THE DRAWINGS

Figure 1:
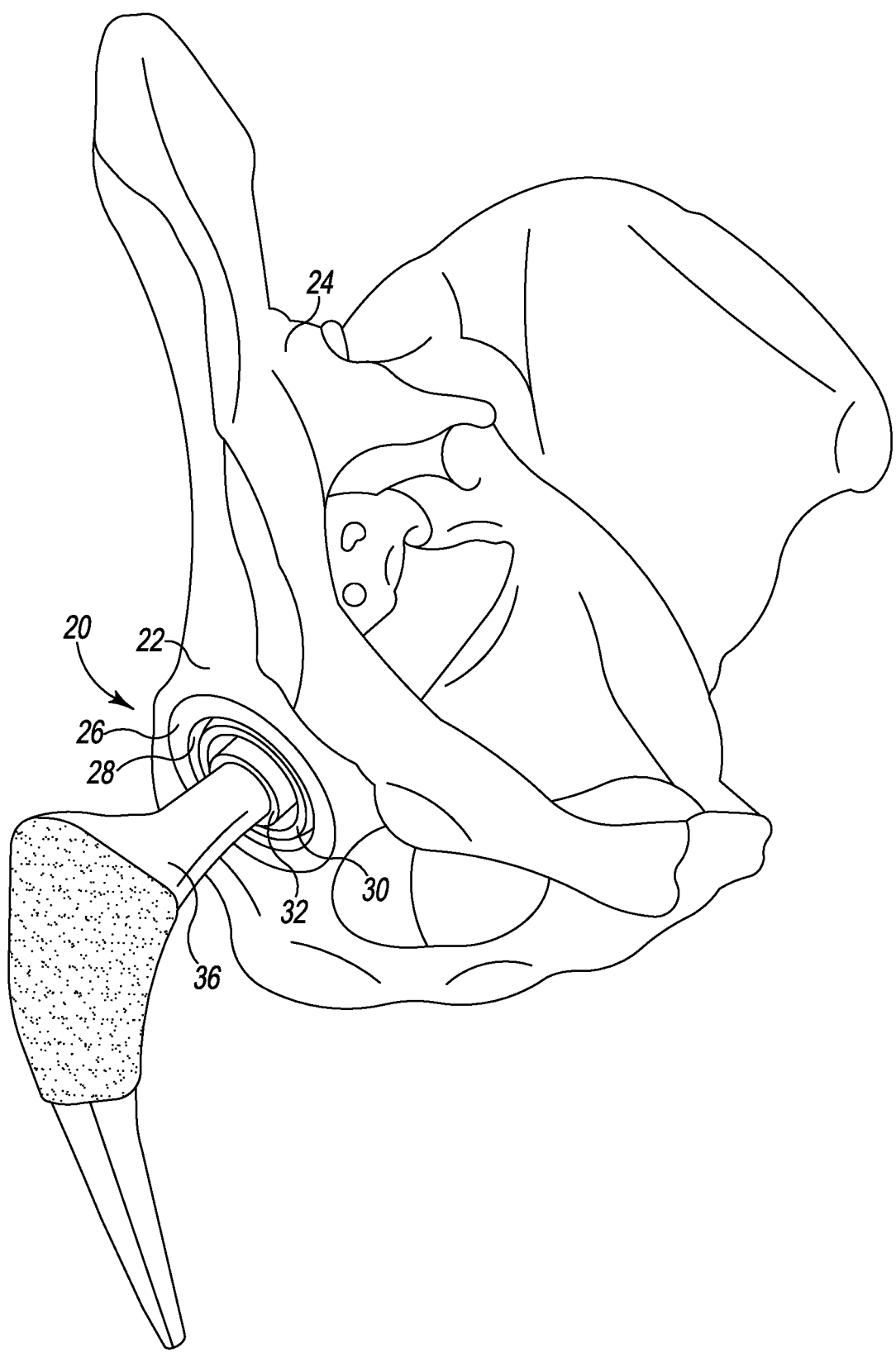
FIG. 1 is a perspective view showing an acetabular hip implant installed within an acetabulum of a patient's hip along with a corresponding femoral component.

While the concepts of the present disclosure are susceptible to various modifications and alternative forms, specific exemplary embodiments thereof have been shown by way of example in the drawings and will herein be described in detail. It should be understood, however, that there is no intent to limit the concepts of the present disclosure to the particular forms disclosed, but on the contrary, the intention is to cover all modifications, equivalents, and alternatives falling within the spirit and scope of the invention as defined by the appended claims.

Terms representing anatomical references, such as anterior, posterior, medial, lateral, superior, inferior, etcetera, may be used throughout this disclosure in reference to both the orthopaedic implants described herein and a patient's natural anatomy. Such terms have well-understood meanings in both the study of anatomy and the field of orthopaedics. Use of such anatomical reference terms in the specification and claims is intended to be consistent with their well-understood meanings unless noted otherwise.

Figure 2:
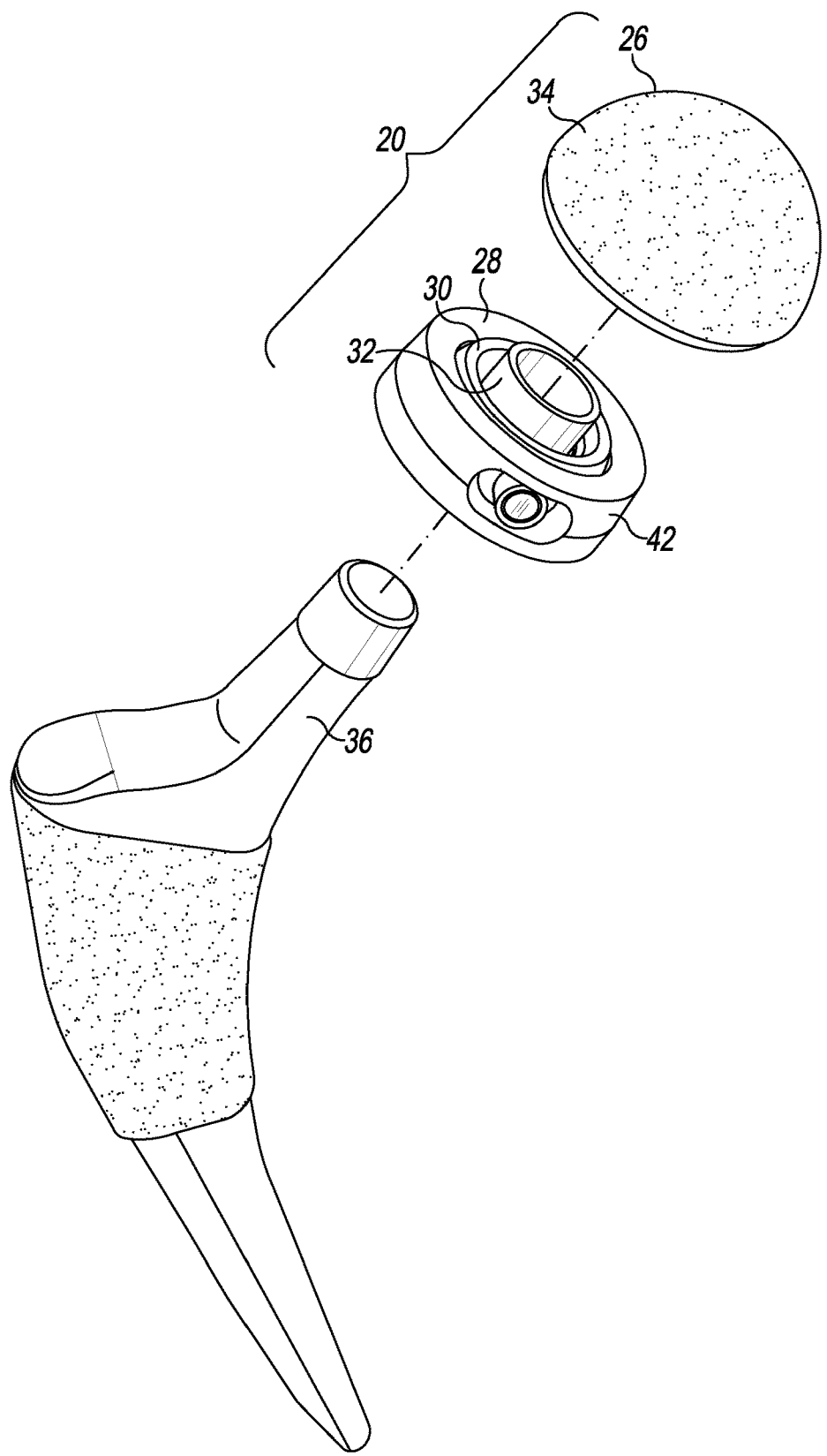
FIG. 2 is an exploded perspective view of the acetabular hip implant and the femoral component of FIG. 1.

Referring now to FIGS. 1 and 2, an acetabular hip implant 20 is shown implanted within an acetabulum 22 of a patient's pelvic bone 24. The acetabular hip implant 20 includes an acetabular shell component 26, an outer ring 28, a middle ring 30, and an inner ring 32. The outer ring 28 is configured to be received within and secured to the acetabular shell component 26, the middle ring 30 is configured to be received within and secured to the outer ring 28, and the inner ring 32 is configured to be received within and secured to the middle ring 30, as will be described in greater detail hereinafter. The inner ring 32 is configured to be secured to a femoral component 36, which is configured to be implanted in the intramedullary canal of the patient's femur (not shown).

In the exemplary embodiment described herein, the rings 28, 30, 32 are constructed with a biocompatible metal that allows for smooth articulation between opposing surfaces of the respective rings. Examples of such biocompatible metals include stainless steel, cobalt chrome, or titanium, although other metals or alloys may be used. The rings 28, 30, 32 may also be made of any suitable medical-grade polymeric material. Examples of such polymeric materials include polyetheretherketone (PEEK), ultrahigh molecular weight polyethylene (UHMWPE), or acetal.

As seen in FIGS. 1 and 2, the acetabular shell component 26 includes an outer surface 34 having a generally rounded shape that is hemispherical or at least partially spherical. The outer surface 34 is configured to be implanted within the acetabulum 22 using any method or structure known in the art. The acetabular shell component 26 further includes an inner surface (not shown) that is partially spherical in shape. An outer surface 42 of the outer ring 28 is taper locked to the acetabular shell component 26.

The acetabular shell component 26 may be constructed of any combination of metal, ultra-high molecular weight polyethylene (UHMWPE), ceramic, polyetheretherketone (PEEK), or any other suitable biomedical material. In one exemplary embodiment, the acetabular shell component 26 is constructed of a higher hardness alloy, such as an alloy of cobalt and chromium, for example CoCrMo. The outer ring 28 may be taper-locked, molded, or otherwise secured to the metal shell. The outer surface 34 of the acetabular shell component 26 may include a coating that promotes ingrowth of bone tissue. For example, the outer surface 34 of the metal shell may have a porous structure in the form of a coating of cobalt-chromium alloy beads. The outer surface 34 of the metal shell may also have a coating of an additional or alternative material that promotes bone ingrowth, such as a hydroxyapatite material.

Figure 3:
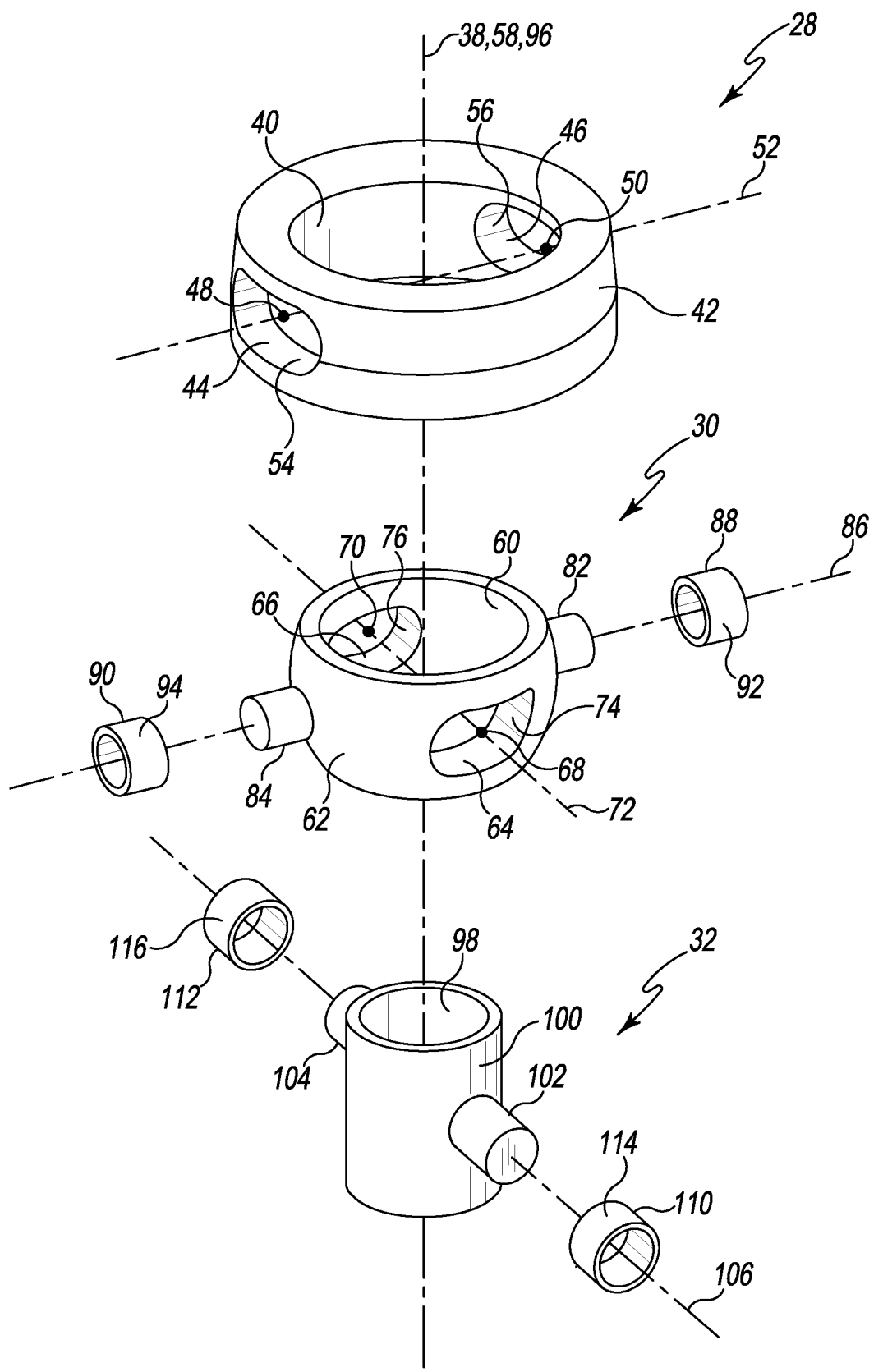
FIG. 3 is an exploded perspective view of the rings of the acetabular hip implant of FIG. 1.
Figure 4:
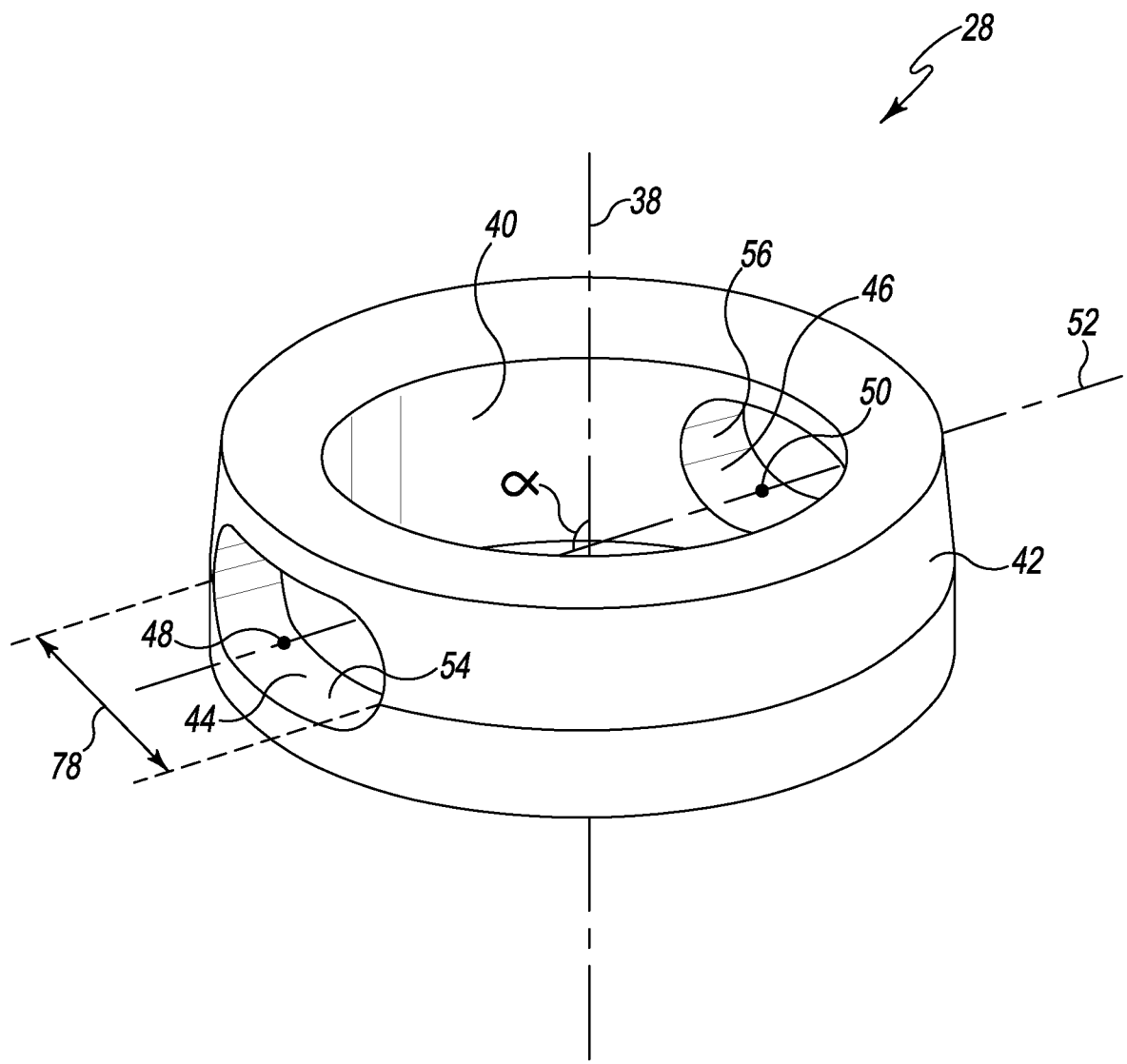
FIG. 4 is a perspective view of the outer ring of the acetabular hip implant of FIG. 1.

The outer ring 28, as shown in FIGS. 3 and 4, extends circumferentially around a longitudinal axis 38. It should be appreciated that the longitudinal axis 38 of the outer ring 28 is collinear with the longitudinal axes 58, 96 of the middle ring 30 and the inner ring 32, respectively, when the rings 28, 30, 32 are secured to one another. The outer ring 28 includes an inner surface 40 facing the longitudinal axis 38 and an outer surface 42 positioned opposite the inner surface 40. The outer ring 28 includes a pair of elongated slots in the form of closed tracks 44, 46. The closed track 44 extends circumferentially around the outer ring 28 and radially through the inner surface 40 and the outer surface 42 thereof. Likewise, the closed track 46 also extends circumferentially around the outer ring 28 and radially through the inner surface 40 and the outer surface 42 thereof.

The closed track 46 is located opposite the closed track 44, as shown in FIGS. 3 and 4. The closed track 44 has a midpoint of circumferential extension 48, and the closed track 46 has a midpoint of circumferential extension 50. An imaginary line 52 extends through the midpoints of circumferential extension 48, 50 of the closed tracks 44, 46. In the exemplary embodiment described herein, when the closed tracks 44, 46 are viewed in cross-sectional planes perpendicular to the imaginary line 52, the imaginary line 52 extends through the center of mass, or centroid, of the two-dimensional shape defined by the closed tracks 44, 46. As such, the imaginary line 52 defines the longitudinal axis of the shape formed by the inner walls 54, 56 of each of the closed tracks 44, 46, respectively.

As shown in FIG. 4, an angle α is formed between the imaginary line 52 (and therefore, the longitudinal axis of the shape defined by the inner walls 54, 56) and the longitudinal axis 38 of the outer ring 28. In the exemplary embodiment described herein, the imaginary line 52 is perpendicular to the longitudinal axis 38 of the outer ring 28. In other illustrative embodiments, the imaginary line 52 is non-orthogonal to the longitudinal axis 38 of the outer ring 28, and, as such, the angle α may be a non-right angle. In some embodiments, the angle α may be a customized, patient-specific angle and may be determined prior to implanting the acetabular hip implant 20 in the patient.

Figure 5:
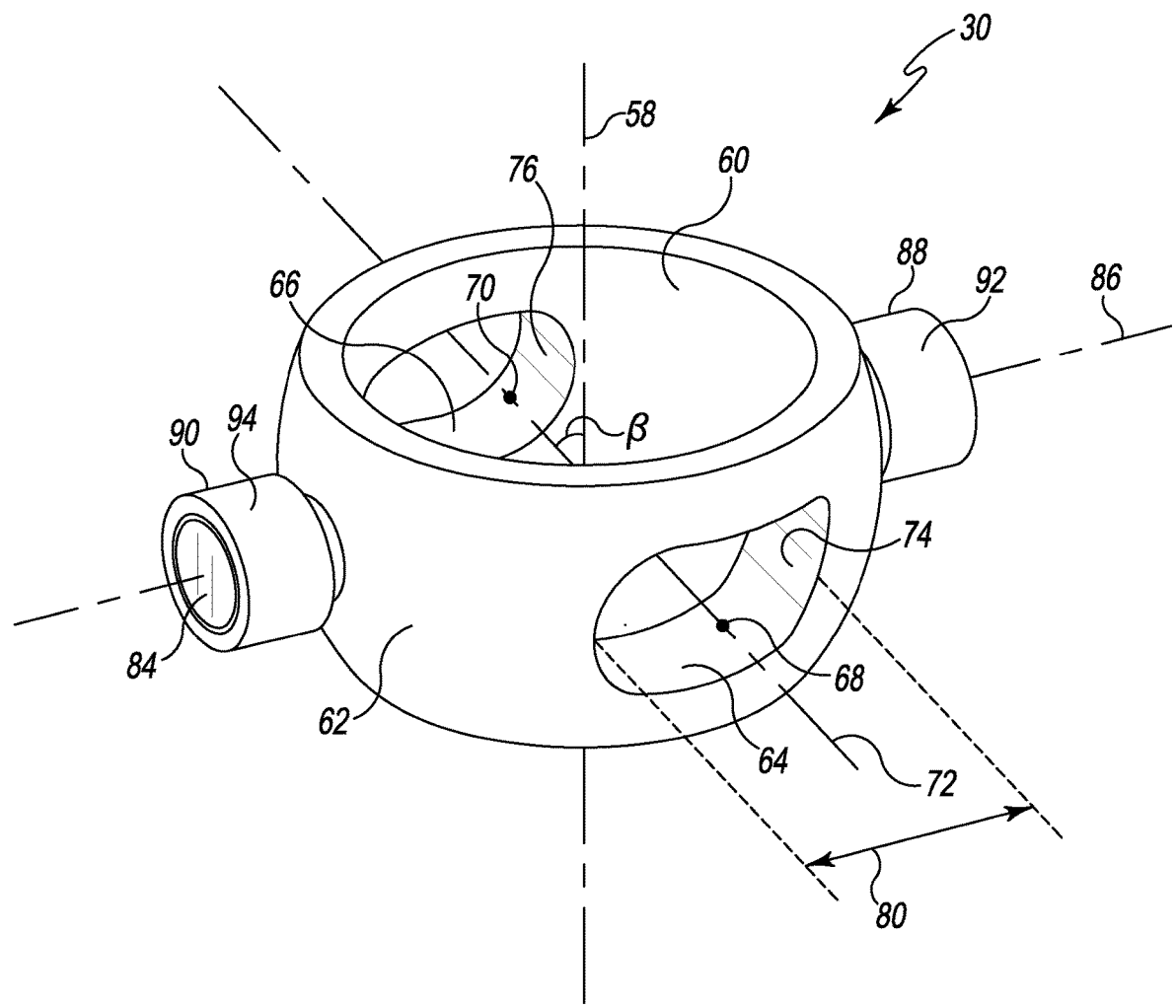
FIG. 5 is a perspective view of the middle ring of the acetabular hip implant of FIG. 1.

The middle ring 30, as shown in FIGS. 3 and 5, extends circumferentially around a longitudinal axis 58. It should be appreciated that the longitudinal axis 58 of the middle ring 30 is collinear with the longitudinal axis 38, 96 of the outer ring 28 and the inner ring 32, respectively, when the rings 28, 30, 32 are secured to one another. The middle ring 30 includes an inner surface 60 facing its longitudinal axis 58 and an outer surface 62 positioned opposite the inner surface 60. In the illustrative embodiment described herein, the inner surface 60 is substantially cylindrical in shape, with the outer surface 62 having a convex curvature. The surfaces 60, 62 are shaped to facilitate interaction with the outer and inner rings 28, 32, as discussed in greater detail below.

Similarly to the outer ring 28, the middle ring 30 also includes a pair of elongated slots in the form of closed tracks 64, 66. The closed track 64 extends circumferentially around the middle ring 30 and radially through the inner surface 60 and the outer surface 62 thereof. In a similar manner, the closed track 66 also extends circumferentially around the middle ring 30 and radially through the inner surface 60 and the outer surface 62 of the middle ring 30.

The closed track 64 is located opposite the closed track 66, as shown in FIGS. 3 and 5. The closed track 64 has a midpoint of circumferential extension 68, and the closed track 66 has a midpoint of circumferential extension 70. An imaginary line 72 extends through the midpoints of circumferential extension 68, 70 of the closed tracks 64, 66. When the closed tracks 64, 66 are viewed in cross-sectional planes perpendicular to the imaginary line 72, the imaginary line 72 extends through the center of mass, or centroid, of the two-dimensional shape defined by the closed tracks 64, 66. As such, the imaginary line 72 defines the longitudinal axis of the shape defined by the inner walls 74, 76 of each of the closed tracks 64, 66, respectively.

As shown in FIG. 5, an angle β is formed between the imaginary line 72 (and therefore, the longitudinal axis of the shape defined by the inner walls 74, 76) and the longitudinal axis 58 of the middle ring 30. In the exemplary embodiment described herein, the imaginary line 72 is perpendicular to the longitudinal axis 58 of the middle ring 30. In other illustrative embodiments, the imaginary line 72 is non-orthogonal to the longitudinal axis 58 of the middle ring 30, and, as such, the angle β may be a non-right angle. In some embodiments, the angle β may be a customized, patient-specific angle and may be determined prior to implanting the acetabular hip implant 20 in the patient.

As described above, each elongated slot/track 44, 46, 64, 66 is embodied as a closed track. That is, unlike an open track that is open on one or both of its ends, the tracks are 44, 46, 64, 66 are closed on both ends and, as such, do not extend around the full circumference of the ring or open into each other. As such, the closed tracks 44, 46 are discrete from one another, and similarly, the closed tracks 64, 66 are discrete from one another.

As shown in FIGS. 3 and 5, the closed tracks 44, 46 extend circumferentially around the outer ring 28 a distance 78, and the closed tracks 64, 66 extend circumferentially around the middle ring 30 a distance 80. In some embodiments, the distance 78 is equal to the distance 80. In some embodiments, the distance 78 is a customized and predetermined, patient-specific distance based on a desired range of motion for a particular patient's hip when the acetabular hip implant 20 is implanted in the acetabulum 22 of the patient. In some embodiments, the distance 80 is likewise a customized and predetermined, patient-specific distance based on a desired range of motion for a particular patient's hip when the acetabular hip implant 20 is implanted in the acetabulum 22 of the patient.

The middle ring 30, as best seen in FIGS. 3 and 5, includes a pair of pins 82, 84 extending radially outward from the outer surface 62 thereof. The pin 82 and the pin 84 extend away from one another along a first rotational axis 86. In the exemplary embodiment described herein, the body of the middle ring 30 and the pins 82, 84 are embodied as a monolithic metallic component constructed with a biocompatible metal. Alternatively, the body of the middle ring 30 and the pins 82, 84 may be embodied as discrete components secured to one another. In such an embodiment, the body of the middle ring 30 and the pins 82, 84 may be constructed with the same biocompatible metal or polymer or differing biocompatible metals or polymers. Examples of such biocompatible metals and polymers were discussed above.

As shown in FIGS. 3 and 5, a pair of bearing sleeves 88, 90 is secured to the pins 82, 84, respectively, of the middle ring 30. The bearing sleeves 88, 90 may be secured to the pins 82, 84, for example, by press fitting the bearing sleeves 88, 90 onto the pins 82, 84. The bearing sleeves 88, 90 are sized and shaped such that the bearing sleeves 88, 90 may be positioned in the closed tracks 44, 46, respectively, of the outer ring 28. In the exemplary embodiment described herein, the bearing sleeves 88, 90 are made of any suitable medical-grade polymeric material that allows for smooth articulation between the outer surfaces 92, 94 of the bearing sleeves and the inner walls 54, 56 of the closed tracks 44, 46 of the outer ring 28. Examples of such polymeric materials include polyetheretherketone (PEEK), ultrahigh molecular weight polyethylene (UHMWPE), or acetal.

When the middle ring 30 is secured to the outer ring 28, the pin 82 (along with its bearing sleeve 88) extends into, and is captured within, the closed track 44. Likewise, the pin 84 (along with its bearing sleeve 90) extends into, and is captured within, the closed track 46. When so assembled, the middle ring 30 is operable to rotate relative to the outer ring 28 about both the rotational axis 86 and the longitudinal axis 38, 58 (as noted above, the axes 38, 58 are collinear when the rings 28, 30 are secured to one another). In the case of rotation of the middle ring 30 relative to the outer ring 28 about the longitudinal axis 38, 58, the middle ring 30 is permitted to move back and forth along an arcuate path defined by the length of the closed tracks 44, 46. Specifically, the middle ring 30 is permitted to rotate relative to the outer ring 28 about the longitudinal axis 38, 58 until the pin 82 (along with its bearing sleeve 88) contacts one end of the closed track 44 at which point the pin 84 (along with its bearing sleeve 90) contacts the opposite end of the closed track 46. Conversely, the middle ring 30 is permitted to rotate relative to the outer ring 28 about the longitudinal axis 38, 58 in the opposite direction until the pin 82 (along with its bearing sleeve 88) contacts the opposite end of the closed track 44 at which point the pin 84 (along with its bearing sleeve 90) contacts the opposite end of the closed track 46. In other words, the length of the closed tracks 44, 46 define the degree/range of rotation permitted by the middle ring 30 relative to the outer ring 28 about the longitudinal axis 38, 58.

It should be appreciated that as the middle ring 30 rotates relative to the outer ring 28 about the longitudinal axis 38, 58, the rotational axis 86 moves in an imaginary plane extending perpendicular to the longitudinal axis 38, 58. As such, in the exemplary embodiment described herein, the rotational axis 86 remains perpendicular to the longitudinal axis 38, 58 throughout movement of the middle ring 30 relative to the outer ring 28. However, it should be appreciated that in other embodiments in which the imaginary line 52 (see FIGS. 3 and 4) forms a non-orthogonal angle α with the longitudinal axis 38, 58, the rotational axis 86 is not perpendicular to the longitudinal axis 38, 58 when the middle ring 30 is secured to the outer ring 28.

In regard to rotation of the middle ring 30 relative to the outer ring 28 along the rotational axis 86, the configuration of the surfaces of the rings 28, 30 creates a predetermined range/degree of rotation between the two rings. Specifically, the outer surface 62 of the middle ring 30 is configured to abut the inner surface 40 of the outer ring 28 at predetermined locations so as to limit rotation of the middle ring 30 about the rotational axis 86 to a predetermined range/degree of rotation relative to the outer ring 28. As such, the convex curvature of the outer surface 62 of the middle ring 30 facilitates rotation of the middle ring 30 about the rotational axis 86 while maintaining a constant degree of spacing between the outer surface 62 of the middle ring 30 and the inner surface 40 of the outer ring 28. It should be appreciated that the contour and thickness of the middle ring 30 may be a customized, patient-specific surface to produce a desired range of motion for a given patient's hip when the acetabular hip implant 20 is implanted in the acetabulum 22 of the patient. For example, depending on the contour of the outer surface 62 of the middle ring 30, increasing the thickness thereof reduces the predetermined range/degree of rotation of the middle ring 30.

As can be seen in FIGS. 2 and 3, the pins 82, 84 (and their associated bearing sleeves 88, 90) are tightly captured within the closed tracks 44, 46. In particular, the pins 82, 84 (and their associated bearing sleeves 88, 90) are sized and shaped to closely correspond to the size and shape of the inner walls 54, 56 of the closed tracks 44, 46 such that the middle ring 30 is prevented from rotating or otherwise moving relative to the outer ring 28 about any additional axis beyond the rotational axis 86 and the longitudinal axis 38, 58.

Figure 6:
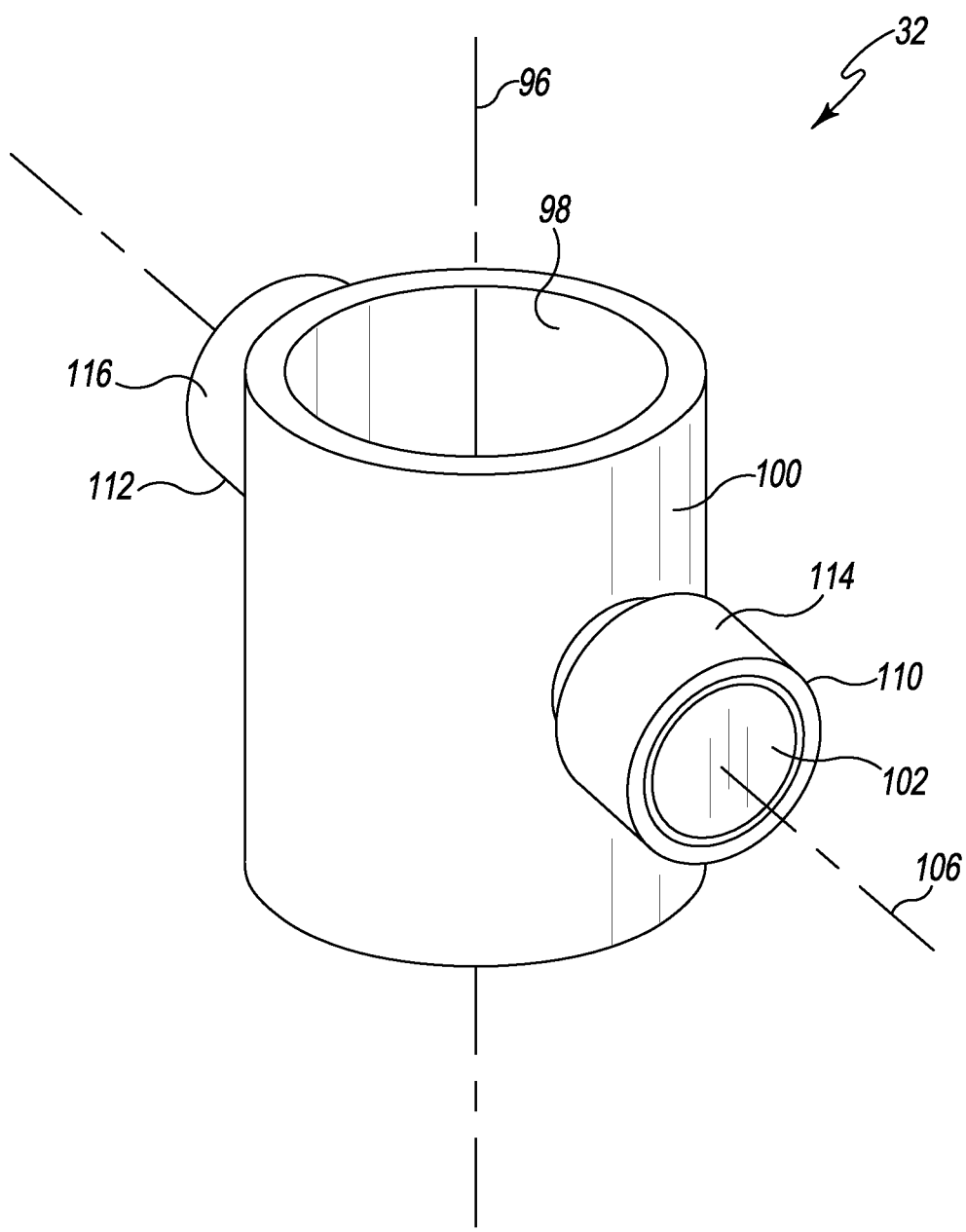
FIG. 6 is a perspective view of the inner ring of the acetabular hip implant of FIG. 1.

The inner ring 32, as shown in FIGS. 3 and 6, extends circumferentially around a longitudinal axis 96. It should be appreciated that the longitudinal axis 96 of the inner ring 32 is collinear with the longitudinal axis 38, 58 of the outer ring 28 and the middle ring 30, respectively, when the rings 28, 30, 32 are secured to one another. The inner ring 32 includes an inner surface 98 facing its longitudinal axis 96 and an outer surface 100 positioned opposite the inner surface 98.

The inner ring 32 includes a pair of pins 102, 104 extending radially outward from the outer surface 100 of the inner ring 32. The pins 102, 104 extend away from one another along a second rotational axis 106. In the exemplary embodiment described herein, the body of the inner ring 32 and the pins 102, 104 are embodied as a monolithic metallic component constructed with a biocompatible metal. Alternatively, the body of the inner ring 32 and the pins 102, 104 may be embodied as discrete components secured to one another. In such an embodiment, the body of the inner ring 32 and the pins 102, 104 may be constructed with the same biocompatible metal or polymer or differing biocompatible metals or polymers. Examples of such biocompatible metals and polymers were discussed above.

As shown in FIGS. 3 and 6, a pair of bearing sleeves 110, 112 is secured to the pins 102, 104, respectively, of the inner ring 32. The bearing sleeves 110, 112 may be secured to the pins 102, 104, for example, by press fitting the bearing sleeves 110, 112 onto the pins 102, 104. The bearing sleeves 110, 112 are sized and shaped such that the bearing sleeves 110, 112 may be positioned in the closed tracks 64, 66, respectively, of the inner ring 30. In the exemplary embodiment described herein, the bearing sleeves 110, 112 are made of any suitable medical-grade polymeric material that allows for smooth articulation between outer surfaces 114, 116 of the bearing sleeves and the inner walls 74, 76 of the closed tracks 64, 66 of the middle ring 30. Examples of such polymeric materials include polyetheretherketone (PEEK), ultrahigh molecular weight polyethylene (UHMWPE), or acetal.

When the inner ring 32 is secured to the middle ring 30, the pin 102 (along with its bearing sleeve 110) extends into, and is captured within, the closed track 64. Likewise, the pin 104 (along with its bearing sleeve 112) extends into, and is captured within, the closed track 66. When so assembled, the inner ring 32 is operable to rotate relative to the middle ring 30 about both the rotational axis 106 and the longitudinal axis 38, 58, 96 (note, as alluded to above, the axes 38, 58, 96 are collinear when the rings 28, 30, 32 are secured to one another). In the case of rotation of the inner ring 32 relative to the middle ring 30 about the longitudinal axis 38, 58, 96, the inner ring 32 is permitted to move back and forth along an arcuate path defined by the length of the closed tracks 64, 66 of the middle ring 30. Specifically, the inner ring 32 is permitted to rotate relative to the middle ring 30 about the longitudinal axis 38, 58, 96 until the pin 102 (along with its bearing sleeve 110) contacts one end of the closed track 64 at which point the pin 104 (along with its bearing sleeve 112) contacts the opposite end of the closed track 66. Conversely, the inner ring 32 is permitted to rotate relative to the middle ring 30 about the longitudinal axis 38, 58, 96 in the opposite direction until the pin 102 (along with its bearing sleeve 110) contacts the opposite end of the closed track 64 at which point the pin 104 (along with its bearing sleeve 112) contacts the opposite end of the closed track 66. In other words, the length of the closed tracks 64, 66 defines the range/degree of rotation permitted by the inner ring 32 relative to the middle ring 30 about the longitudinal axis 38, 58, 96.

It should be appreciated that as the inner ring 32 rotates relative to the middle ring 30 about the longitudinal axis 38, 58, 96, the rotational axis 106 moves in an imaginary plane extending perpendicular to the longitudinal axis 38, 58, 96. As such, in the exemplary embodiment described herein, the rotational axis 106 remains perpendicular to the longitudinal axis 38, 58, 96 throughout movement of the inner ring 32 relative to the middle ring 30. However, it should be appreciated that in other embodiments in which the imaginary line 72 (see FIGS. 3 and 5) forms a non-orthogonal angle β with the longitudinal axis 38, 58, 96, the rotational axis 106 is not perpendicular to the longitudinal axis 38, 58, 96 when the inner ring 32 is secured to the middle ring 30.

In regard to rotation of the inner ring 32 relative to the middle ring 30 along the rotational axis 106, the configuration of the surfaces of the rings 30, 32 creates a predetermined range/degree of rotation between the two rings. Specifically, the outer surface 100 of the inner ring 32 is configured to abut the inner surface 60 of the middle ring 30 at predetermined locations so as to limit rotation of the inner ring 32 about the rotational axis 106 to a predetermined range/degree of rotation relative to the middle ring 30. As such, the curvature and configuration of the outer surface 100 of the inner ring 32 facilitates rotation of the inner ring 32 about the rotational axis 106 while maintaining a constant degree of spacing between the outer surface 100 of the inner ring 32 and the inner surface 60 of the middle ring 30. It should be appreciated that the contour and thickness of the inner ring 32 may be a customized, patient-specific surface to produce a desired range of motion for a given patient's hip when the acetabular hip implant 20 is implanted in the acetabulum 22 of the patient. For example, depending on the contour of the outer surface 100 of the inner ring 32, increasing the thickness thereof reduces the predetermined range/degree of rotation of the inner ring 32.

The pins 102, 104 (and their associated bearing sleeves 110, 112) are tightly captured within the closed tracks 64, 66. In particular, the pins 102, 104 (and their associated bearing sleeves 110, 112) are sized and shaped to closely correspond to the size and shape of the inner walls 74, 76 of the closed tracks 64, 66 such that the inner ring 32 is prevented from rotating or otherwise moving relative to the middle ring 30 about any additional axis beyond the rotational axis 106 and the longitudinal axis 38, 58, 96.

In use during a surgical procedure, the acetabular shell component 26 is first implanted into the acetabulum 22 of the patient. To do so, a reamer (not shown) may be used to ream or otherwise cut the acetabulum 22 in order to form a hemispherically shaped cavity. The surgeon may then install either the final acetabular shell component or, more commonly, a trial component. Trialing assists the surgeon in final preparation of the acetabulum 22 and in choosing the proper sizes of the various components of the acetabular hip implant 20. After suitable trialing, the trial component is removed and the surgeon may then implant the acetabular shell component 26 into the acetabulum 22. The acetabular shell component 26 may be press fit, screwed, cemented, or otherwise attached to the acetabulum 22.

Thereafter, the outer ring 28 of the assembled ring assembly is taper-locked or otherwise secured to the implanted acetabular shell component 26. Once the ring assembly is secured to the implanted acetabular shell component 26 in such a manner, both the acetabular shell component 26 and the outer ring 28 are stationary relative to one another and hence the acetabulum 22 of the patient. However, both the middle ring 30 and the inner ring 32 are movable relative to the outer ring 28 and the acetabular shell component 26 and hence the acetabulum 22.

The implanted femoral stem 36 is then taper-locked or otherwise locked to the inner ring 32 so as to secure it to the acetabular shell component 26.

Although the rings 28, 30, 32 are herein described as being assembled to one another prior to being secured to the implanted acetabular shell component 26, it should be appreciated that some or all of the rings 28, 30, 32 may be assembled in vivo. Moreover, it should also be appreciated that the rings 28, 30, 32 may be assembled to the acetabular shell component 26 prior to implanting the shell component 26 into the patient's acetabulum 22.

As alluded to above, the acetabular hip implant 20 may be embodied as a customized, patient-specific implant. To do so, the surgeon or other care provider would first determine a desired range of motion for a given patient's hip. After doing so, customized, patient-specific versions of one or more of the rings 28, 30, 32 may be fabricated or selected from a kit of variously configured rings. Customized, patient-specific versions of the rings 28, 30, 32 may be fabricated by, for example, altering the length of a given ring's closed tracks. As described above, the length of the closed tracks defines the range/degree of motion of the relative movement along the longitudinal axis 38, 58, 96 of a given ring relative to another. The angle of the closed tracks may also be varied to create differing directions of rotation. Moreover, the outer and inner surface profiles and/or thicknesses of one or more of the rings may be altered to vary the range/degree of rotation relative to the rotational axis 86 and/or the rotational axis 106.

As such, to assemble a customized, patient-specific version of the acetabular hip implant 20, customized, patient-specific versions of one or more of the rings 28, 30, 32 are assembled based on the desired range of motion for a given patient's hip as preoperatively determined by the surgeon. Thereafter, the rings are secured to an acetabular shell component 26 implanted within the acetabulum 22 of the patient. A stem component may then be secured to the inner ring 32 of the customized, patient-specific acetabular hip implant 20.

As will become apparent from reading the present specification, any of the features of any of the embodiments disclosed herein may be incorporated within any of the other embodiments without departing from the scope of the present disclosure.

While the disclosure has been illustrated and described in detail in the drawings and foregoing description, such an illustration and description is to be considered as exemplary and not restrictive in character, it being understood that only illustrative embodiments have been shown and described and that all changes and modifications that come within the spirit of the disclosure are desired to be protected.

For example, although the outer and middle rings 28, 30 are described herein as having closed tracks and the middle and inner rings 30, 32 are described as having pins, some or all of such elements may be reversed. For example, in some embodiments, the outer and middle rings 28, 30 may have pins extending from the outer surfaces thereof with the middle and inner rings 30, 32 having closed tracks extending radially therethrough.

There are a plurality of advantages of the present disclosure arising from the various features of the apparatus, system, and method described herein. It will be noted that alternative embodiments of the apparatus, system, and method of the present disclosure may not include all of the features described yet still benefit from at least some of the advantages of such features. Those of ordinary skill in the art may readily devise their own implementations of the apparatus, system, and method that incorporate one or more of the features of the present invention and fall within the spirit and scope of the present disclosure.

The invention claimed is:

1. An acetabular hip implant comprising:
an acetabular shell component configured to be implanted within an acetabulum of a patient,
a first ring extending around a first longitudinal axis and secured to the acetabular shell component, the first ring including an inner surface and an outer surface and defining (i) a first closed track extending circumferentially around the first ring and radially through the inner surface and the outer surface of the first ring, and (ii) a second closed track located opposite the first closed track and extending circumferentially around the first ring and radially through the inner surface and the outer surface of the first ring,
a second ring extending around a second longitudinal axis and including an inner surface, an outer surface, a first pin extending from the second ring along a first rotational axis into the first closed track, and a second pin extending from the second ring along the first rotational axis into the second closed track, the second ring defining (i) a third closed track extending circumferentially around the second ring and radially through the inner surface and the outer surface of the second ring, and (ii) a fourth closed track extending circumferentially around the second ring and radially through the inner surface and the outer surface of the second ring,
a third ring extending around a third longitudinal axis and including a third pin extending from the third ring along a second rotational axis into the third closed track and a fourth pin extending from the third ring along the second rotational axis into the fourth closed track.

2. The acetabular hip implant of claim 1, wherein the third ring is secured to a femoral stem component.

3. The acetabular hip implant of claim 1, wherein the second ring is (i) operable to rotate relative to the first ring about the first rotational axis and the first longitudinal axis and (ii) prevented from rotating relative to the first ring about any additional axis.

4. The acetabular hip implant of claim 1, wherein the third ring is (i) operable to rotate relative to the second ring about the second rotational axis and the second longitudinal axis and (ii) prevented from rotating relative to the second ring about any additional axis.

5. The acetabular hip implant of claim 1, wherein the first closed track and the second closed track each extend circumferentially around the first ring a first distance, and wherein the third closed track and the fourth closed track each extend circumferentially around the second ring a second distance.

6. The acetabular hip implant of claim 5, wherein the first distance is a predetermined, patient-specific distance based on a desired range of motion for a patient's hip when the acetabular hip implant is implanted in the acetabulum of the patient.

7. The acetabular hip implant of claim 5, wherein the second distance is a predetermined, patient-specific distance based on a desired range of motion for a patient's hip when the acetabular hip implant is implanted in the acetabulum of the patient.

8. The acetabular hip implant of claim 5, wherein the first distance is equal to the second distance.

9. The acetabular hip implant of claim 1, further comprising (i) a first pair of sleeves configured to be secured to the first and second pins and sized and shaped to be positioned in the first and second closed tracks, and (ii) a second pair of sleeves configured to be secured to the third and fourth pins and sized and shaped to be positioned in the third and fourth closed tracks.

10. The acetabular hip implant of claim 1, wherein the outer surface of the first ring is taper locked to the acetabular shell component.

11. The acetabular hip implant of claim 1, wherein an inner surface of the third ring is taper locked to the femoral stem component.

12. An acetabular hip implant comprising:
an acetabular shell component configured to be implanted within an acetabulum of a patient,
a first ring extending around a first longitudinal axis and secured to the acetabular shell component,
a second ring extending around a second longitudinal axis, the second ring (i) operable to rotate relative to the first ring about the first longitudinal axis and a first rotational axis perpendicular to the first longitudinal axis and (ii) prevented from rotating relative to the first ring about any additional axis, and
a third ring extending around a third longitudinal axis, the third ring (i) operable to rotate relative to the second ring about the second longitudinal axis and a second rotational axis perpendicular to the second longitudinal axis and (ii) prevented from rotating relative to the second ring about any additional axis.

13. The acetabular hip implant of claim 12, wherein the third ring is secured to a femoral stem component.

14. The acetabular hip implant of claim 12, wherein the first ring includes an inner surface defining an inner diameter of the first ring and an outer surface opposite the inner surface,
wherein the second ring includes an inner surface defining an inner diameter of the second ring and an outer surface defining an outer diameter of the second ring that is less than the inner diameter of the first ring, and
wherein the third ring includes an inner surface and an outer surface opposite the inner surface and defining an outer diameter of the third ring that is less than the inner diameter of the second ring.

15. The acetabular hip implant of claim 14, wherein the first ring defines a first pair of closed tracks extending circumferentially around the first ring a first distance and radially through the inner surface and the outer surface of the first ring, and the second ring defines a second pair of closed tracks extending circumferentially around the second ring a second distance and radially through the inner surface and the outer surface of the second ring.

16. The acetabular hip implant of claim 15, wherein the first distance is a predetermined, patient-specific distance based on a desired range of motion for a patient's hip when the acetabular hip implant is implanted in the acetabulum of the patient.

17. The acetabular hip implant of claim 15, wherein the second distance is a predetermined, patient-specific distance based on a desired range of motion for a patient's hip when the acetabular hip implant is implanted in the acetabulum of the patient.

18. The acetabular hip implant of claim 15, wherein the second ring includes a first pair of pins extending from the outer surface of the second ring along the first rotational axis into the first pair of closed tracks, and the third ring includes a second pair of pins extending from the outer surface of the third ring along the second rotational axis into the second pair of closed tracks.

19. A method of fabricating a customized patient-specific acetabular hip implant comprising:
   determining a desired range of motion for a patient's hip,
   selecting a first ring having a first pair of closed tracks defined therein and extending circumferentially around the first ring a first patient-specific distance, the first patient-specific distance based on the desired range of motion for the patient's hip,
   selecting a second ring having a second pair of closed tracks defined therein and extending circumferentially around the second ring a second patient-specific distance, the second patient-specific distance based on the desired range of motion for the patient's hip,
   securing the second ring to the first ring,
   securing a third ring of the customized, patient-specific acetabular hip implant to the second ring, and
   securing the first ring to an acetabular shell component configured to be implanted within the acetabulum of the patient.

20. The method of claim 19, further comprising:
   securing a stem component to the third ring of the customized, patient-specific acetabular hip implant.

* * * * *